(12) United States Patent
Old et al.

(10) Patent No.: US 8,362,054 B2
(45) Date of Patent: Jan. 29, 2013

(54) THERAPEUTIC SUBSTITUTED LACTAMS

(75) Inventors: David W. Old, Irvine, CA (US); Wha Bin Im, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/527,155

(22) PCT Filed: Feb. 8, 2008

(86) PCT No.: PCT/US2008/053386
§ 371 (c)(1),
(2), (4) Date: Feb. 23, 2010

(87) PCT Pub. No.: WO2008/100809
PCT Pub. Date: Aug. 21, 2008

(65) Prior Publication Data
US 2010/0168189 A1    Jul. 1, 2010

Related U.S. Application Data

(60) Provisional application No. 60/890,181, filed on Feb. 15, 2007.

(51) Int. Cl.
*A61K 31/4025* (2006.01)
*A61K 31/41* (2006.01)
*C07D 409/12* (2006.01)
*C07D 403/12* (2006.01)

(52) U.S. Cl. ........ 514/381; 514/422; 548/527; 548/252; 548/254

(58) Field of Classification Search .................. None
See application file for complete search history.

(56) References Cited

U.S. PATENT DOCUMENTS

2006/0205800 A1    9/2006   Donde et al.

FOREIGN PATENT DOCUMENTS

| WO | WO 2006/096829 | 9/2006 |
| WO | WO 2006/098918 | 9/2006 |
| WO | WO 2007/109578 | 9/2007 |

OTHER PUBLICATIONS

"Side Reactions in Organic Synthesis: A Guide to Successful Synthesis Design", Wiley-VCH Verlag GmbH & Co. KGaA, Weinheim, pp. 1-16 (2005).*
U.S. Appl. No. 10/599,046, filed Jun. 29, 2007, David W. Old, et al.
U.S. Appl. No. 11/553,143, filed Oct. 26, 2006, Yariv Donde, et al.
Silverman, Richard B., The Organic Chemistry of Drug Design and Drug Action, 2nd Edition, Amsterdam: Elsevier Academic Press, 2004, p. 29.
Han et. al. (Biorganic & Medicinal Chemistry Letters 15 (2005) 3487-3490).
Orlek et al. (J. Med. Chem. 1991, 34, 2726-2735).
Andersen et al. (Eur. J. Med. Chem. 1996, 31, 417-425).
Kohara et al. (J. Med. Chem. 1996, 39, 5228-5235).
Drysdale et al. (J. Med. Chem. 1992, 35, 2573-2581).
(Francis A. Carey, Organic Chemistry, New York: McGraw-Hill Book Company 1987, p. 63).
RIGO; "Studies on Pyrrolidinones, Synthesees of 5-(5-oxy-2-pyrrolidinyl)-1,2,4-triazole-3-thinone Derivatives"; 1989 J Heterocyclic Chem 26 1723.

* cited by examiner

*Primary Examiner* — Michael Barker
(74) *Attorney, Agent, or Firm* — Kevin Forrestal; Krishna G. Banerjee

(57) ABSTRACT

Therapeutic compounds, compositions, methods, and medicaments related thereto are disclosed herein.

19 Claims, No Drawings

THERAPEUTIC SUBSTITUTED LACTAMS

CROSS REFERENCE TO RELATED APPLICATIONS

This is a national stage application under 35 U.S.C. §371 of PCT patent application PCT/2008/053386, filed on Feb. 8, 2008, which claims the benefit of U.S. Provisional Patent Application 60/890,181, filed Feb. 15, 2007, which is hereby incorporated by reference in its entirety.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

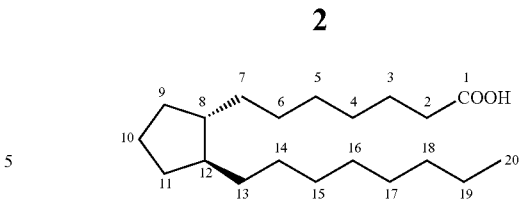

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound of the formula

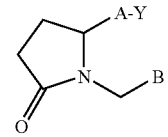

or a pharmaceutically acceptable salt thereof;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH$—$(CH_2)_3$—, or —$CH_2C≡C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—; and B is substituted aryl or heteroaryl.

Also disclosed is a compound of the formula

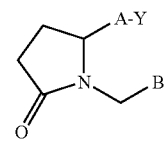

or a pharmaceutically acceptable salt thereof;

Y is carboxylic acid or a bioisostere thereof;

A is —$(CH_2)_6$—, cis —$CH_2CH=CH$—$(CH_2)_3$—, or —$CH_2C≡C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—; and B is substituted aryl or heteroaryl.

These compounds are useful for treating glaucoma or elevated intraocular pressure.

The definitions, explanations, and examples provided in this document shall be used to determine the meaning of a particular term or expression where there is any ambiguity arising from any disclosure incorporated by reference herein.

"Bioisosteres are substituents or groups that have chemical or physical similarities, and which produce broadly similar biological properties." Silverman, Richard B., *The Organic*

*Chemistry of Drug Design and Drug Action*, 2nd Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated for Y. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Bioorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

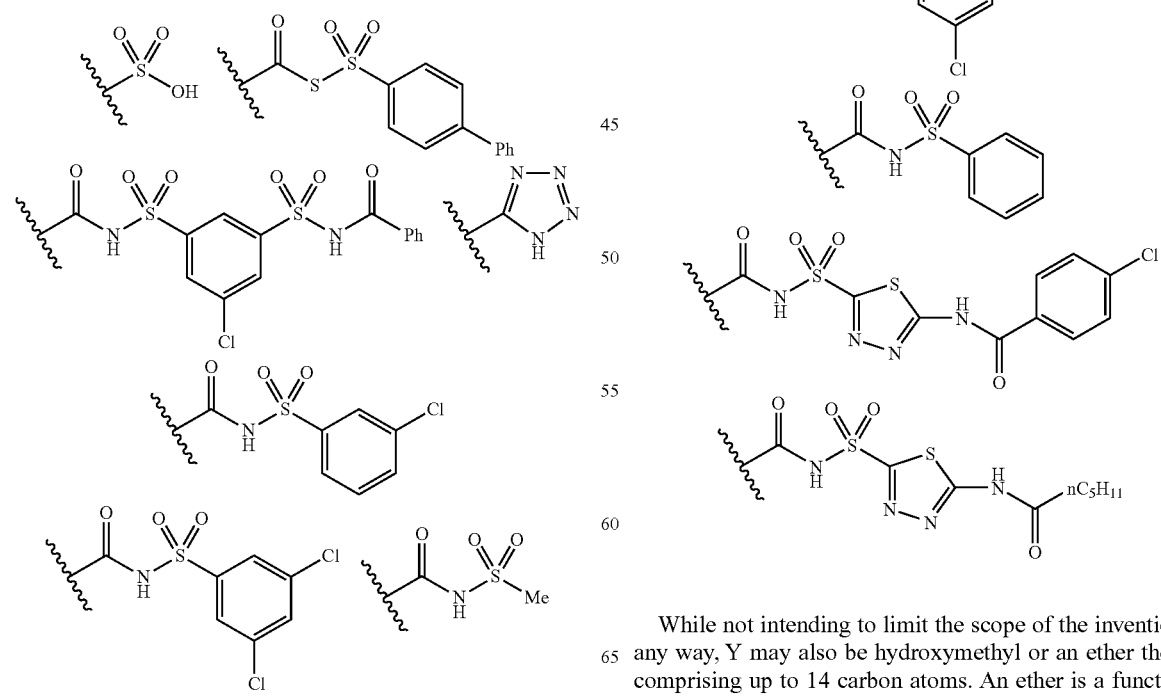

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

Thus, while not intending to be limiting, the structures below exemplify what is meant by tetrazolyl; carboxylic acid, phosphonic acid, sulfonic acid, and their esters and amides; hydroxymethyl and ether of hydroxymethyl. In these structures, R is H or hydrocarbyl, subject to the constraints defined herein.

Each structure below represents a specific embodiment which is individually contemplated, as well as pharmaceutically acceptable salts and prodrugs of compounds which are represented by the structures.

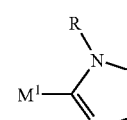

$M^1$ =

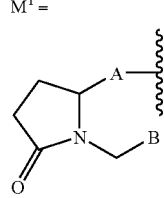

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

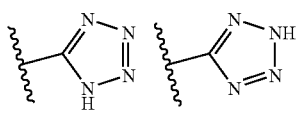

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

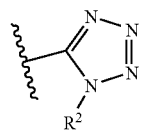

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

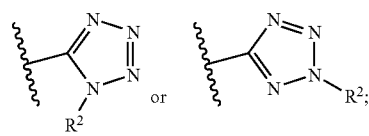

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

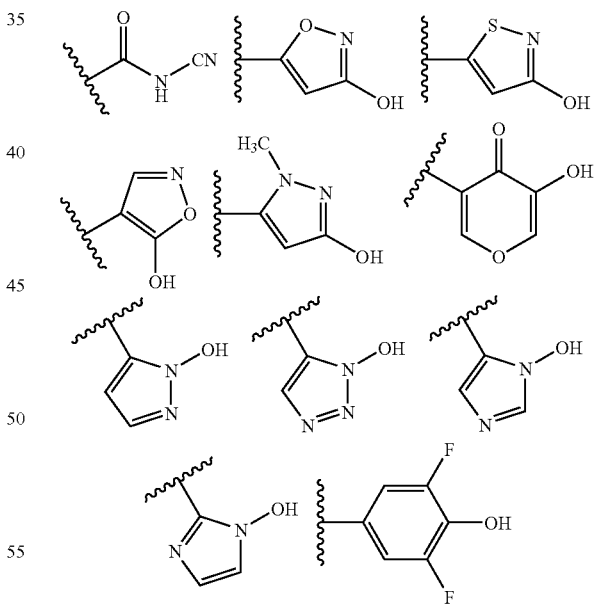

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

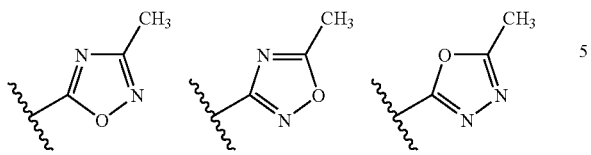

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

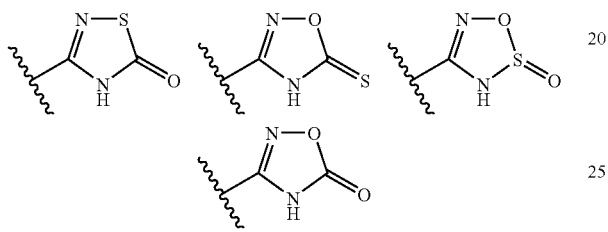

Drysdale et al. (*J. Med. Chem.* 1992, 35, 2573-2581) have described carboxylic acid mimics of non-peptide CCK—B receptor antagonists. The binding affinities of many of the bioisosteres are similar to the parent carboxylic acid.

Carboxylic Acid Bioisosteres According to Drysdale et. al.

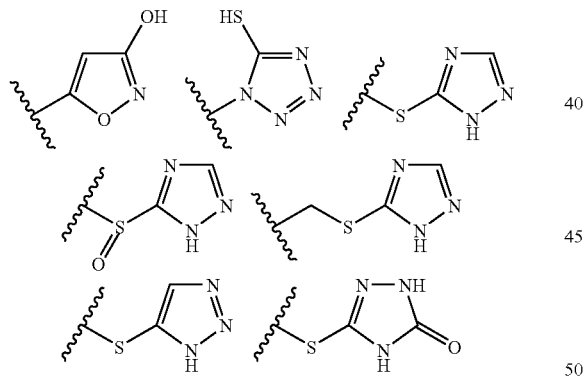

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH=CH— or —C≡C—.

Thus, while not intending to be limiting, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

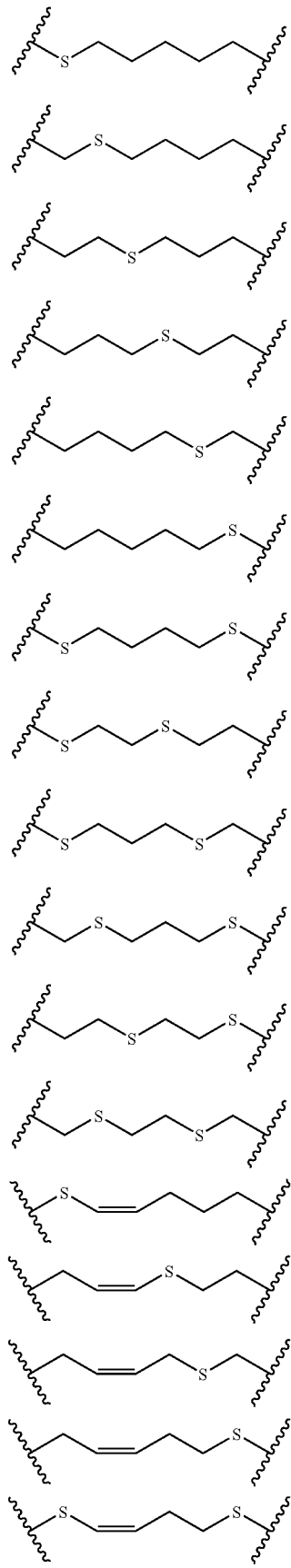

-continued

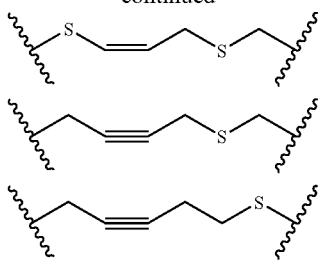

Alternatively, while not intending to limit the scope of the invention in any way, A may be a moiety where O replaces one or two carbon atoms such as one of the following or the like.

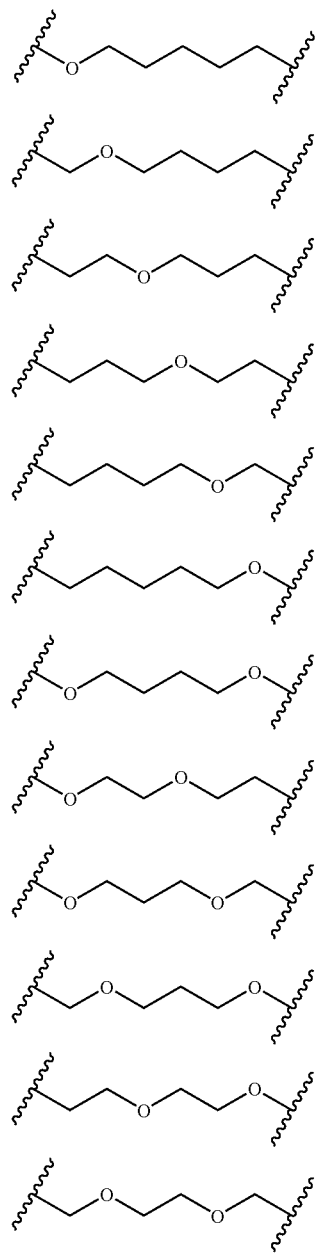

-continued

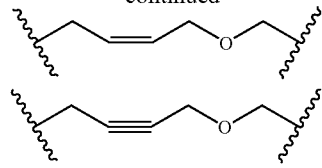

Alternatively, while not intending to limit the scope of the invention in any way, A may have an O replacing one carbon atom and an S replacing another carbon atom, such as one of the following or the like.

Alternatively, while not intending to limit the scope of the invention in any way, in certain embodiments A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—. In other words, while not intending to limit the scope of the invention in any way, in one embodiment A comprises:
1) a) 1, 2, 3, or 4 —$CH_2$— moieties, or
   b) 0, 1 or 2 —$CH_2$— moieties and —CH=CH— or —C≡C—; and
2) Ar;
e.g. —$CH_2$—Ar—, —$(CH_2)_2$—Ar—, —CH=CH—Ar—, —$CH_2$—Ar—$CH_2$—, —$CH_2$Ar—$(CH_2)_2$—, —$CH_2$Ar—CH=CH—, —$CH_2$Ar—C≡C—, —$(CH_2)_2$—Ar—$(CH_2)_2$—, and the like;

in another embodiment A comprises:
1) a) O; and 0, 1, 2, or 3 —$CH_2$— moieties; or
   b) O; and 0 or 1 —$CH_2$— moieties and —CH=CH— or —C≡C—; and
2) Ar;
e.g., —O—Ar—, —Ar—$CH_2$—O—, —O—Ar—$(CH_2)_2$—, —OAr—CH=CH—, —O—Ar—C≡C—, —O—$CH_2$—Ar, —O—$CH_2$—Ar—$(CH_2)_2$, —O—$CH_2$Ar—CH=CH—, —O—$CH_2$Ar—C≡C—, and the like; or in another embodiment A comprises:
1) a) S; and 0, 1, 2, or 3 —CH₂— moieties; or
b) S; and 0 or 1 —CH₂— moieties and —CH=CH— or —C≡C—; and
2) Ar;
e.g., —S—Ar—, —Ar—CH₂—S—, —S—Ar—(CH₂)₂—, —SAr—CH=CH—, —S—CH₂—Ar—(CH₂)₂, —S—CH₂Ar—CH=CH—, —S—CH₂Ar—C≡C—, and the like.

In another embodiment, the sum of m and o is 2, 3, or 4 wherein one CH₂ may be replaced with S or O and 1 —CH₂—CH₂— may be replaced by —CH=CH— or —C≡C—.

In another embodiment, the sum of m and o is 3 wherein one CH₂ may be replaced with S or O and 1 —CH₂—CH₂— may be replaced by —CH=CH— or —C≡C—.

In another embodiment, the sum of m and o is 2 wherein one CH₂ may be replaced with S or O or 1 —CH₂—CH₂— may be replaced by —CH=CH— or —C≡C—.

In another embodiment, the sum of m and o is 4 wherein one CH₂ may be replaced with S or O and 1 —CH₂—CH₂— may be replaced by —CH=CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH₂)₂-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. In addition to the atoms listed above, a substituent may also have a metal cation or any other stable cation having an atom not listed above if the substituent is acidic and the salt form is stable. For example, —OH may form an —O⁻Na⁺ salt or CO₂H may form a CO₂⁻K⁺ salt. Any cation of the salt is not counted in the "4 or less heavy atoms." Thus, the substituent may be hydrocarbyl, i.e. a moiety consisting of only carbon and hydrogen, including linear, branched or cyclic hydrocarbyl, and combinations thereof; having up to 4 carbon atoms, including alkyl up to $O_4$, alkenyl, alkynyl, and the like;

hydrocarbyloxy, i.e. —O-hydrocarbyl, up to $C_3$;

organic acid such as CO₂H, SO₃H, P(O)(OH)₂, and the like, and salts thereof;

CF₃;

halo, such as F, Cl, or Br;

hydroxyl;

NH₂ and alkylamine functional groups up to $C_3$;

other N or S containing substituents such as CN, NO₂, and the like;

and the like.

In one embodiment A is —(CH₂)ₘ-Ph-(CH₂)ₒ— wherein the sum of m and o is 1, 2, or 3, and wherein one CH₂ may be replaced with S or O.

In another embodiment A is —CH₂—Ar—OCH₂—. In another embodiment A is —CH₂-Ph-OCH₂—. In another embodiment, Ph is attached at the 1 and 3 positions, otherwise known as m-interphenylene, such as when A has the structure shown below.

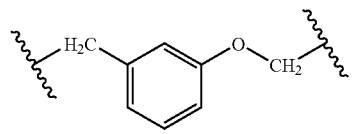 [SMILES: *COc1cccc(C*)c1]

In another embodiment A is —(CH₂)₆—, cis —CH₂CH=CH—(CH₂)₃—, or —CH₂C≡C—(CH₂)₃—, wherein 1 or 2 carbon atoms may be replaced with S or O; or A is —(CH₂)₂-Ph- wherein one —CH₂— may be replaced with S or O.

In another embodiment A is —(CH₂)₆—, cis —CH₂CH=CH—(CH₂)₃—, or —CH₂C≡C—(CH₂)₃—, wherein 1 or 2 carbon atoms may be replaced with S or O; or A is —(CH₂)₂-Ph-.

In one embodiment, Ar is thienyl.

In other embodiments, A has one of the following structures.

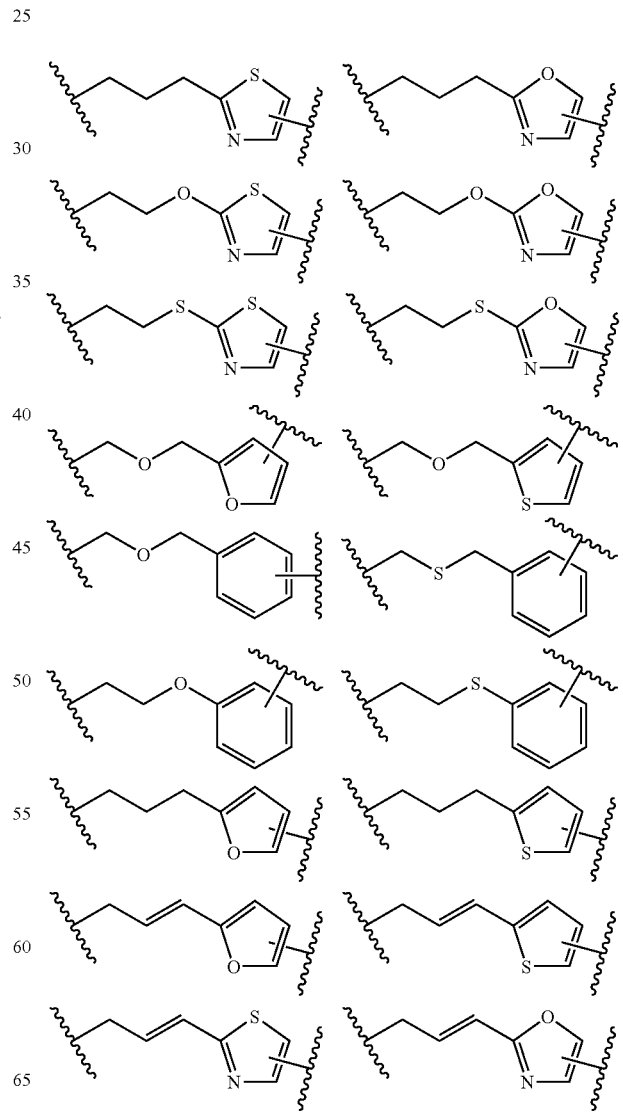

-continued

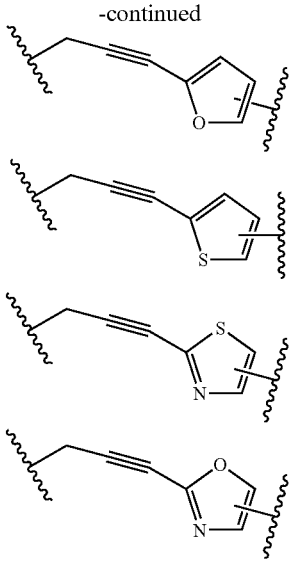

In another embodiment A is —CH₂OCH₂Ar—.
In another embodiment A is —CH₂SCH₂Ar—.
In another embodiment A is —(CH₂)₃Ar—.
In another embodiment A is —CH₂O(CH₂)₄—.
In another embodiment A is —CH₂S(CH₂)₄—.
In another embodiment A is —(CH₂)₆—.
In another embodiment A is cis —CH₂CH═CH—(CH₂)₃—.
In another embodiment A is —CH₂C≡C—(CH₂)₃—.
In another embodiment A is —S(CH₂)₃S(CH₂)₂—.
In another embodiment A is —(CH₂)₄OCH₂—.
In another embodiment A is cis —CH₂CH═CH—CH₂OCH₂—.
In another embodiment A is —CH₂CH≡CH—CH₂OCH₂—.
In another embodiment A is —(CH₂)₂S(CH₂)₃—.
In another embodiment A is —CH₂-Ph-OCH₂—, wherein Ph is interphenylene.
In another embodiment A is —CH₂-mPh-OCH₂—, wherein mPh is m-interphenylene.
In another embodiment A is —CH₂—O—(CH₂)₄—.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.
B is substituted aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl should be stable and may have up to 20 non-hydrogen atoms each and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. In addition to the atoms listed above, a substituent may also have a metal cation or other stable cation having an atom not listed above if the substituent is acidic and the salt form is stable. For example, —OH may form an —O⁻Na⁺ salt or CO₂H may form a CO₂⁻K⁺ salt. Any cation of the salt is not counted in the 20 non-hydrogen atoms. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH₃, OCH₂CH₃, O-cyclohexyl, etc, up to 19 carbon atoms;

other ether substituents such as CH₂OCH₃, (CH₂)₂OCH(CH₃)₂, and the like;

thioether substituents including S-hydrocarbyl and other thioether substituents;

hydronhydrocarbyl, meaning hydrocarbyl-OH, including hydroxyalkyl, such as CH₂OH, C(CH₃)₂OH, etc, up to 19 carbon atoms;

acyl. i.e.

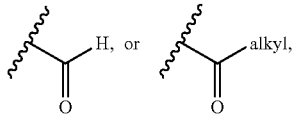

including acetyl, propanyl, and the like;

acyloxy, i.e. —O-acyl, including formate, acetate, propanoate, and the like;

nitrogen substituents such as NO₂, CN, and the like, including amino, such as NH₂, NH(CH₂CH₃OH), NHCH₃, and the like;

carbonyl substituents, such as CO₂H, ester, amide, and the like;

halogen, such as chloro, fluoro, bromo, and the like fluorocarbyl, such as CF₃, CF₂CF₃, etc.;

phosphorous substituents, such as PO₃²⁻, and the like;

sulfur substituents, including S-hydrocarbyl, SH, SO₃H, SO₂-hydrocarbyl, SO₃-hydrocarbyl, and the like.

OH.

Substituents may be the same or different.

In one embodiment, B is phenyl with 1, 2, or 3 substituents.

In another embodiment, at least one substituent of B is C₁₋₃ alkyl, Cl, or F.

In another embodiment, all substituents of B are C₁₋₃ alkyl, Cl, F, or hydroxyalkyl.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

Hydrocarbyl is a moiety consisting of carbon and hydrogen, including, but not limited to:
1. alkyl, which is hydrocarbyl containing no double or triple carbon-carbon bonds; alkyl includes, but is not limited to:
   linear alkyl, cyclic alkyl, branched alkyl, and combinations thereof;
   $C_{1-3}$ alkyl, which refers to alkyl having 1, 2, or 3 carbon atoms, including, but no limited to, methyl, ethyl, isopropyl, cyclopropyl, n-propyl, and the like;
   $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
   combinations of these terms are possible, and their meanings should be obvious to those of ordinary skill in the art; for example $C_{1-6}$ linear alkyl would refer to $C_{1-6}$ alkyl which is also linear;
2. alkenyl, which is hydrocarbyl containing one or more carbon-carbon double bonds; alkenyl includes, but is not limited to:
   linear alkenyl, cyclic alkenyl, branched alkenyl, and combinations thereof;
   alkenyl having 1, 2, 3, or more carbon-carbon double bonds;
3. alkynyl, which is hydrocarbyl containing one or more carbon-carbon triple bonds; akynyl includes, but is not limited to:
   linear alkynyl, cyclic alkynyl, branched alkynyl, and combinations thereof;
   alkynyl having 1, 2, 3, or more carbon-carbon double bonds;
4. aryl, provided that it contains no heteroatoms either in a ring or as a substituent; and
5. combinations of any of the above;

$C_{1-6}$ hydroxylalkyl is hydroxyalkyl having 1, 2, 3, 4, 5, or 6 carbon atoms.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms; and from 0 to 24 hydrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms; 0, 1, 2 or 3 oxygen atoms; and from 0 to 24 hydrogen atoms.

In another embodiment, B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent; said hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

Examples of useful moieties for B are depicted below. Each is individually contemplated as an embodiment.

Structure:

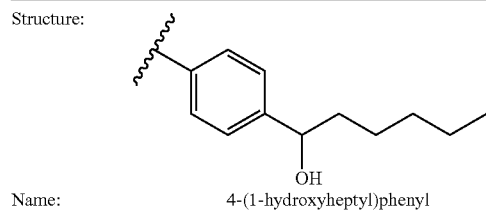 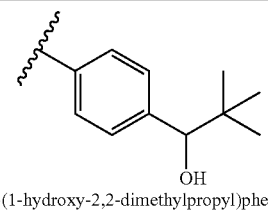

Name: 4-(1-hydroxyheptyl)phenyl     4-(1-hydroxy-2,2-dimethylpropyl)phenyl

Structure:

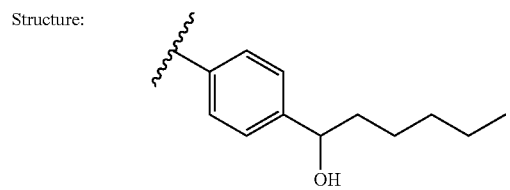 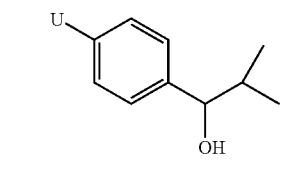

Name: 4-(1-hydroxyhexyl)phenyl     4-(1-hydroxy-2-methylpropyl)phenyl

-continued

| Structure: | 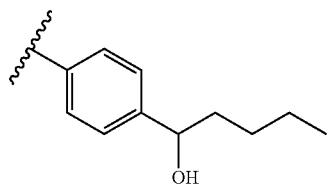 [SMILES: *c1ccc(C(O)CCCC)cc1] | 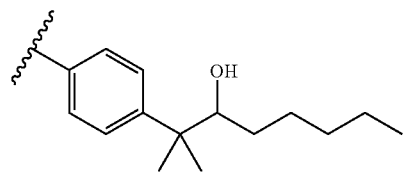 [SMILES: *c1ccc(C(C)(C)C(O)CCCCC)cc1] |
| Name: | 4-(1-hydroxypentyl)phenyl | 4-(3-hydroxy-2-methyloctan-2-yl)phenyl |
| Structure: | 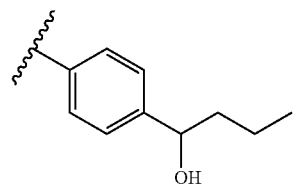 [SMILES: *c1ccc(C(O)CCC)cc1] | 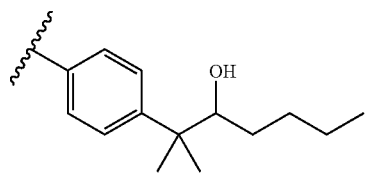 [SMILES: *c1ccc(C(C)(C)C(O)CCCC)cc1] |
| Name: | 4-(1-hydroxybutyl)phenyl | 4-(3-hydroxy-2-methylheptan-2-yl)phenyl |
| Structure: | 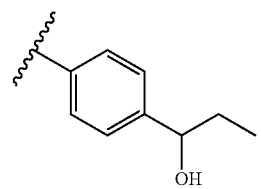 [SMILES: *c1ccc(C(O)CC)cc1] | 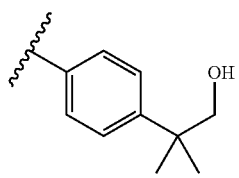 [SMILES: *c1ccc(C(C)(C)CO)cc1] |
| Name: | 4-(1-hydroxypropyl)phenyl | 4-(1-hydroxy-2-methylpropan-2-yl)phenyl |
| Structure: | 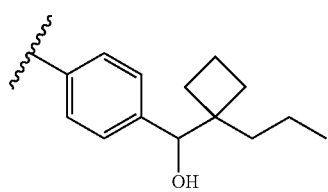 [SMILES: *c1ccc(C(O)C2(CCC)CCC2)cc1] | 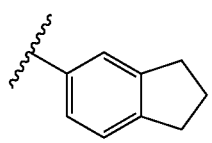 [SMILES: *c1ccc2c(c1)CCC2] |
| Name: | 4-(hydroxy(1-propylcyclobutyl)methyl)phenyl | 2,3-dihydro-1H-inden-5-yl |
| Structure: | 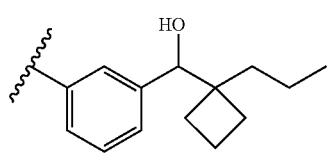 [SMILES: *c1cccc(C(O)C2(CCC)CCC2)c1] | 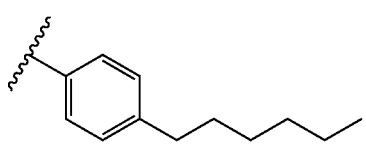 [SMILES: *c1ccc(CCCCCC)cc1] |
| Name: | 3-(hydroxy(1-propylcyclobutyl)methyl)phenyl | 4-hexylphenyl |
| Structure: | 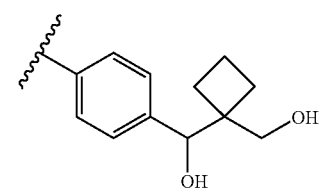 [SMILES: *c1ccc(C(O)C2(CO)CCC2)cc1] | 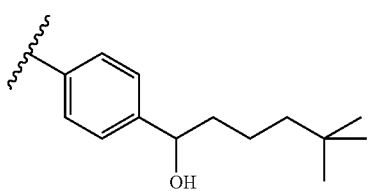 [SMILES: *c1ccc(C(O)CCCC(C)(C)C)cc1] |
| Name: | 4-(hydroxy(1-(hydroxymethyl)cyclobutyl)methyl)phenyl | 4-(1-hydroxy-5,5-dimethylhexyl)phenyl |
| Structure: | 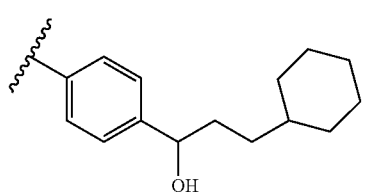 [SMILES: *c1ccc(C(O)CCC2CCCCC2)cc1] | 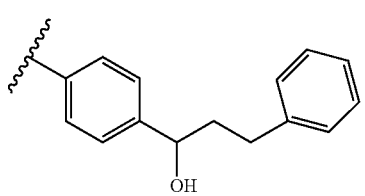 [SMILES: *c1ccc(C(O)CCc2ccccc2)cc1] |
| Name: | 4-(3-cyclohexyl-1-hydroxypropyl)phenyl | 4-(1-hydroxy-3-phenylpropyl)phenyl |

-continued

| Structure: | | |
|---|---|---|
| | 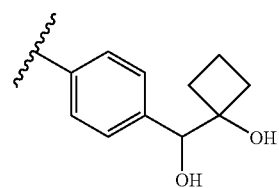 [SMILES: *c1ccc(C(O)C2(O)CCC2)cc1] | 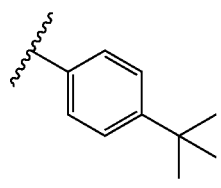 [SMILES: *c1ccc(C(C)(C)C)cc1] |
| Name: | 4-(hydroxy(1-hydroxycyclobutyl)methyl)phenyl | 4-tert-butylphenyl |
| Structure: | 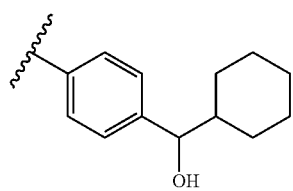 [SMILES: *c1ccc(C(O)C2CCCCC2)cc1] | 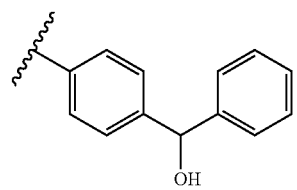 [SMILES: *c1ccc(C(O)c2ccccc2)cc1] |
| Name: | 4-(cyclohexyl(hydroxy)methyl)phenyl | 4-(hydroxy(phenyl)methyl)phenyl |
| Structure: | 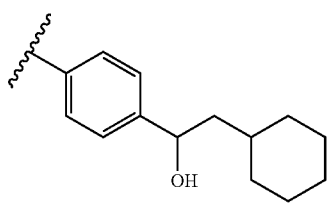 [SMILES: *c1ccc(C(O)CC2CCCCC2)cc1] | 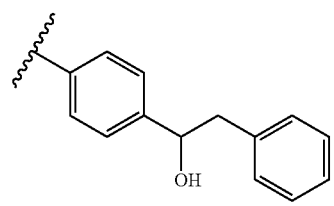 [SMILES: *c1ccc(C(O)Cc2ccccc2)cc1] |
| Name: | 4-(2-cyclohexyl-1-hydroxyethyl)phenyl | 4-(1-hydroxy-2-phenylethyl)phenyl |
| Structure: | 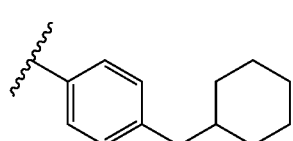 | 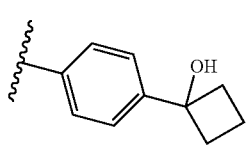 [SMILES: *c1ccc(C2(O)CCC2)cc1] |
| Name: | 4-(cyclohexylmethyl)phenyl | 4-(1-hydroxycyclobutyl)phenyl |
| Structure: | 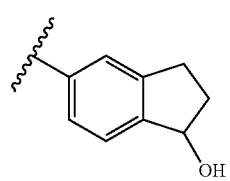 [SMILES: *c1ccc2c(c1)CCC2O] | 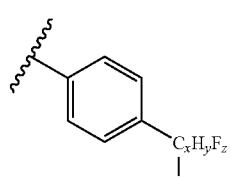 |
| Name: | 1-hydroxy-2,3-dihydro-1H-inden-5-yl | |
| Structure: | 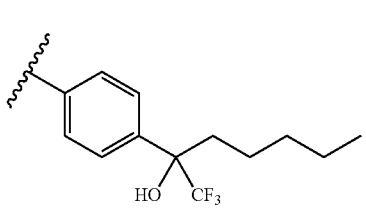 [SMILES: *c1ccc(C(O)(CCCCC)C(F)(F)F)cc1] | 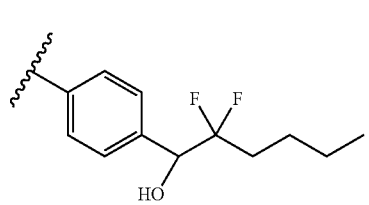 [SMILES: *c1ccc(C(O)C(F)(F)CCCC)cc1] |
| Name: | 4-(1,1,1-trifluoro-2-hydroxyheptan-2-yl)phenyl | 4-(2,2-difluoro-1-hydroxyhexyl)phenyl |
| structure: | 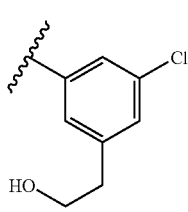 [SMILES: *c1cc(Cl)cc(CCO)c1] | 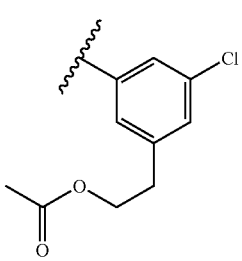 [SMILES: *c1cc(Cl)cc(CCOC(C)=O)c1] |
| name: | 3-chloro-5-(2-hydroxyethyl)phenyl | 3-(2-acetoxyethyl)-5-chlorophenyl |

| structure: | 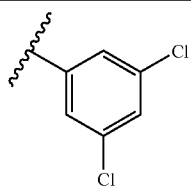 | 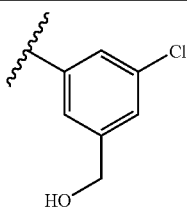 |
|---|---|---|
| name: | 3,5-dichlorophenyl | 3-chloro-5-(hydroxymethyl)phenyl |
| structure: | 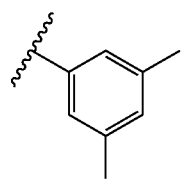 [SMILES: *c1cc(C)cc(C)c1] | 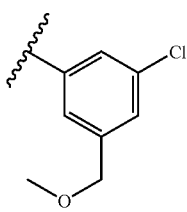 [SMILES: *c1cc(Cl)cc(COC)c1] |
| name: | 3,5-dimethylphenyl | 3-chloro-5-(methoxymethyl)phenyl |

In the above embodiments, x is 5, 6, or 7, and y+z is 2x+1.

In one embodiment, x is 5 and y+z is 11.

In another embodiment, x is 6 and y+z is 13.

In another embodiment, x is 7 and y+z is 15.

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

The term aromatic refers to the meaning commonly understood in the art, i.e. it refers to an unsaturated, fully conjugated ring having 4N+2 ring electrons (e.g. 2, 6, 10, etc.) Thus, phenyl, pyridinyl, thienyl, furyl, and the like are aromatic. Aryl is a moiety that is aromatic.

A heavy atom is an atom which is not hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

Unless otherwise indicated, reference to a compound should be construed broadly to include pharmaceutically acceptable salts and prodrugs of the depicted structure.

Unless stereochemistry is explicitly depicted, a structure is intended to include every possible stereoisomer, both pure or in any possible mixture. In particular, compounds having the stereochemistry indicated in the structure below are contemplated.

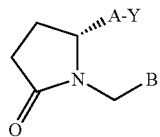

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer."

For the purposes of this disclosure, "treat," "treating," or "treatment" refer to the use of a compound, composition, therapeutically active agent, or drug in the diagnosis, cure, mitigation, treatment, prevention of disease or other undesirable condition.

The compounds disclosed herein are useful in the manufacture of a medicament for the treatment of glaucoma or elevated intraocular pressure in a mammal.

Another embodiment is a composition comprising a compound disclosed herein, wherein said composition is a liquid which is ophthalmically acceptable.

Another embodiment is a medicament comprising a compound disclosed herein, wherein said medicament is a liquid which is ophthalmically acceptable.

Another embodiment is a method comprising administering a compound disclosed herein to a mammal for the treatment of glaucoma or elevated intraocular pressure.

Another embodiment is a kit comprising a composition comprising compound disclosed herein, a container, and instructions for administration of said composition to a mammal for the treatment of glaucoma or elevated intraocular pressure.

Methods of formulating compounds such as those disclosed herein for ophthalmic and other pharmaceutical preparations are well known in the art. For example, U.S. patent application Ser. No. 10/599,046, incorporated by reference herein, filed on Sep. 18, 2006, describes typical formulation methods.

Synthetic Methods

Scheme 1

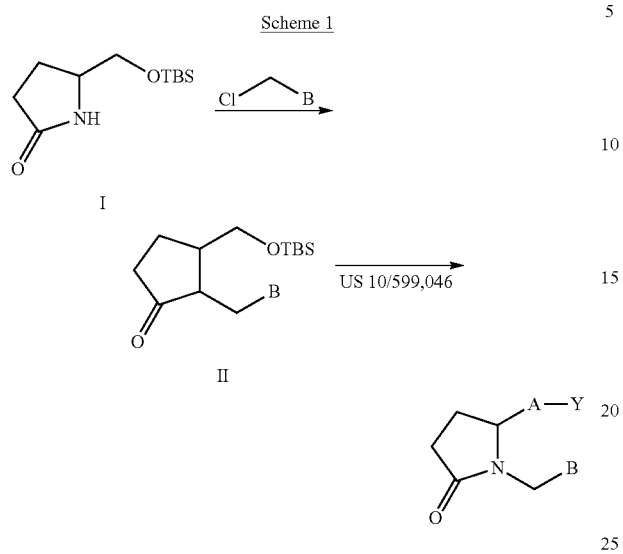

While there are a number of potential methods of making the compounds disclosed herein, one possible general strategy is outlined in Scheme 1 above. The chloromethylaryl compounds Cl—CH$_2$—B is added to the nitrogen of the Compound I using a base to form Compound II. Many of these compounds are available commercially, and many more are easily prepared from commercially available compounds using methods known in the art. Other halomethylaryl compounds might be used, as well as other leaving groups such as triflate, tosylate, etc. Compound II can then be converted to the claimed compounds by converting the —CH$_2$—OTBS group to A. A number of methods of doing this transformation are known in the art. For example, U.S. patent application Ser. No. 10/599,046 describes a procedure that may be adapted to yield the desired compounds with a variety of A groups.

Scheme 2 describes the synthesis of one exemplary compound (5) that has been prepared.

Scheme 2

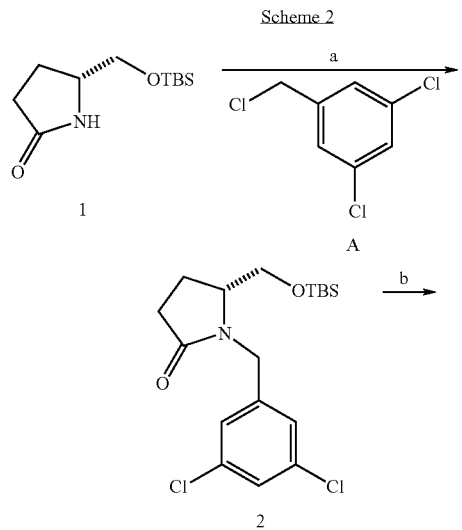

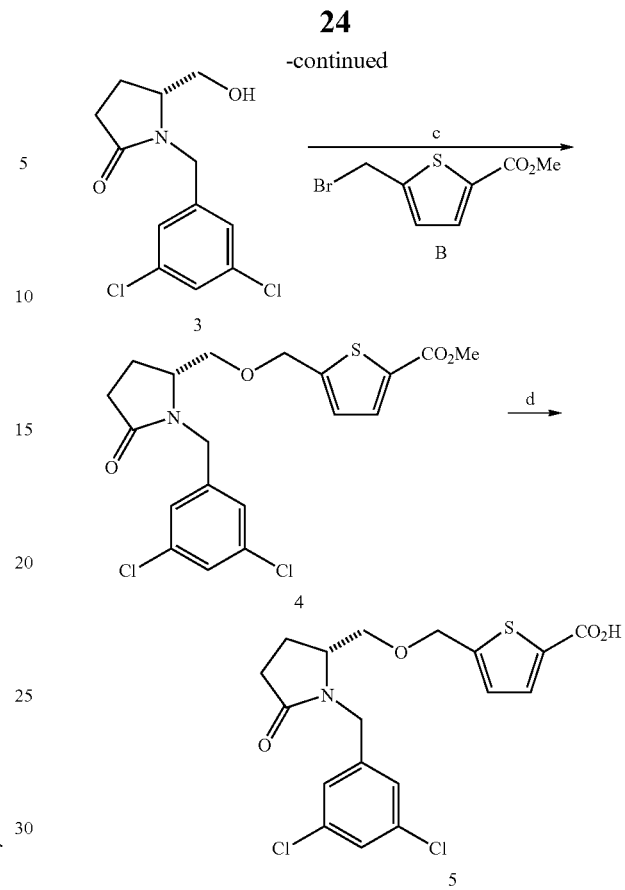

(a) NaH, TBAI, A, DMF; (b) TBAF, THF; (c) NaH, B, DMF; (d) LiOH, H$_2$O, THF.

(R)-5-(((1-(3,5-dichlorobenzyl)-5-oxopyrrolidin-2-yl)methoxy)methyl)thiophene-2-carboxylic acid (5)

Step 1. Alkylation of 1 with A to Give 2

Sodium hydride (40 mg of a 60% dispersion in oil, 1.0 mmol) was added to a solution of 1 (200 mg, 0.87 mmol) in DMF (5 mL). After 30 min at room temperature, a solution of A (commercially available from Acros Chemical, 187 mg, 0.96 mmol) in DMF (3.7 mL) was added, followed by tetrabutylammonium iodide (32 mg, 0.087 mmol). The mixture was heated at 40° C. for 18 h then cooled to room temperature. The mixture was partitioned between EtOAc (50 mL) and water (50 mL). The phases were separated and the aqueous phase was extracted with EtOAc (2×20 mL). The combined organic phase was washed with brine (50 mL), dried (MgSO$_4$), filtered and concentrated in vacuo. The crude residue was purified by flash column chromatography on 12 g silica (hexane→EtOAc, gradient) to afford 70 mg (21%) of 2.

Step 2. Deprotection of 2 to Give 3

Tetrabutylammonium fluoride (0.54 mL of a 1.0 M solution in THF, 0.54 mmol) was added to a solution of 2 (70 mg, 0.18 mmol) in THF (1.0 mL) at room temperature. After 18 h at room temperature the mixture was diluted with EtOAc (15 mL), washed with water (2×15 mL) and brine (10 mL), dried (MgSO$_4$), filtered and concentrated in vacuo. The crude residue was purified by flash column chromatography on 4 g silica (hexane→EtOAc, gradient) to afford 40 mg (81%) of 3.

Step 3. Alkylation of 3 with B to Give 4

Sodium hydride (9 mg of a 60% dispersion in oil, 0.23 mmol) was added to a solution of 3 (40 mg, 0.15 mmol) in DMF (0.36 mL) at 0° C. The mixture was allowed to warm to room temperature. After 30 min at room temperature, a solution of B (see U.S. Provisional Patent Application No. 60/804,680, filed Jun. 14, 2006, incorporated by reference herein, 29 mg, 0.12 mmol) in DMF (0.36 mL) was added. After 10 min the reaction was partitioned between water (10 mL) and $CH_2Cl_2$ (20 mL). The phases were separated and the aqueous phase was extracted with $CH_2Cl_2$ (2×10 mL). The combined organic phase was dried ($MgSO_4$), filtered and concentrated in vacuo. The crude residue was purified by flash column chromatography on 4 g silica (hexane→EtOAc, gradient) to afford 20 mg (38%) of 4.

Step 4. Saponification of 4 to Give 5

A solution of lithium hydroxide (0.30 mL of a 1.0 M solution in water, 0.30 mmol) was added to a solution of 4 (20 mg, 0.047 mmol) in THF (0.20 mL). The mixture was partitioned between 10% HCl (5 mL) and EtOAc (5 mL). The phases were separated and the aqueous phase was extracted with EtOAc (2×5 mL). The combined extracts were washed with brine (5 mL), dried ($MgSO_4$), filtered and concentrated in vacuo.

The crude residue was purified by flash column chromatography on 4 g silica (10% $MeOH/CH_2Cl_2$) to afford 11 mg (57%) of 5.

In Vitro Testing

U.S. patent application Ser. No. 11/553,143, filed on Oct. 26, 2006, incorporated by reference herein, describes the methods used to obtain the in vitro data in the table below.

1 —$CH_2$— may be replaced by S or O, and 1 —$CH_2$—$CH_2$— may be replaced by —CH=CH— or —C≡C—; and B is substituted aryl or heteroaryl, wherein all substituents of aryl or heteroaryl independently have from 1 to 20 non-hydrogen atoms independently selected from C, N, O, S, P, F, Cl, Br, and I.

2. The compound of claim 1 having a formula

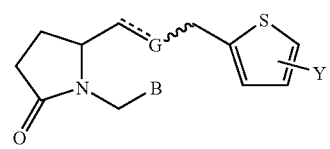

or a pharmaceutically acceptable salt thereof; wherein a dashed line indicates the presence or absence of a bond; and G is —CH—, —$CH_2$—, O, or S.

3. The compound of claim 2 wherein G is O.

4. The compound of claim 2 wherein G is —$CF1_2$—.

5. The compound of claim 1 wherein B is substituted phenyl.

6. The compound of claim 5 wherein B is dichlorophenyl.

7. The compound of claim 2 having a formula

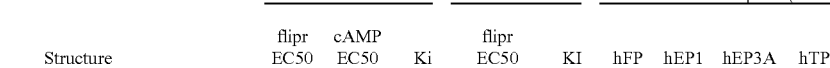

|  | EP2 data | | | EP4 data | | Other Receptors (EC50 in nM) | | | | | |
|---|---|---|---|---|---|---|---|---|---|---|---|
| Structure | flipr EC50 | cAMP EC50 | Ki | flipr EC50 | KI | hFP | hEP1 | hEP3A | hTP | hIP | hDP |
| 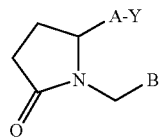 | 8508 | 81 | 2569 | >10000 | 7303 | NA | NA | 6448 | NA | NA | NA |

What is claimed is:

1. A compound having a formula or a pharmaceutically acceptable salt thereof;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH—(CH_2)_3$—, or —$CH_2C≡C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein or a pharmaceutically acceptable salt thereof; wherein $R^a$ is H, alkyl of from 1 to 6 carbon atoms, or phenyl.

8. A method of treating glaucoma or elevated intraocular pressure comprising administering a compound according to claim 1 to a mammal in need thereof.

9. The compound of claim 1, wherein Ar is unsubstituted.

10. The compound of claim 1, wherein Ar has 1 or 2 substituents having from 1 to 4 atoms independently selected from C, N, O, S, P, F, Cl, Br, and I.

11. The compound of claim 10, wherein all substituents of Ar are independently selected from $C_{1-4}$ hydrocarbyl, $C_{1-3}$ hydrocarbyloxy, $CO_2H$, $SO_3H$, $P(O)(OH)_2$, $CF_3$, halo, OH, $NH_2$, $C_{1-3}$ amino, CN, and $NO_2$.

12. The compound of claim 1, wherein all substitutents of B have from 1 to 20 non-hydrogen atoms and are independently selected from hydrocarbyl, ether substituents, thioether substituents, hydroxyhydrocarbyl, acyl, acyloxy, $NO_2$, CN, $NH_2$, amino, $CO_2H$, ester substituents, amide substituents, halo, $CF_3$, $CF_2CF_3$, and OH.

13. The compound of claim 1, wherein each substituent of B has one or more carbon, fluorine, chlorine, bromine, or oxygen atoms; and wherein all substituents taken together consist of 0-10 carbon atoms, 0-9 fluorine atoms, 0-3 chlorine atoms, 0-3 bromine atoms, 0-3 oxygen atoms, and 0-24 hydrogen atoms.

14. The compound of claim 1, wherein all substituents of B are $C_{1-3}$ alkyl, Cl, F, or hydroxylakyl.

15. The compound of claim 1, wherein B is 3,5-dichlorophenyl.

16. The method of claim 8, wherein Ar is unsubstituted, or has 1 or 2 substituents having from 1 to 4 atoms independently selected $C_{1-4}$ hydrocarbyl, $C_{1-3}$ hydrocarbyloxy, $CO_2H$, $SO_3H$, $P(O)(OH)_2$, $CF_3$, halo, OH, $NH_2$, $C_{1-3}$ amino, CN, and $NO_2$.

17. The method of claim 8, wherein all substitutents of B have from 1 to 20 non-hydrogen atoms and are independently selected from hydrocarbyl, ether substituents, hydroxyhydrocarbyl, acyl, acyloxy, CN, $NH_2$, amino, $CO_2H$, ester substituents, amide substituents, F, Cl, Br, $CF_3$, $CF_2CF_3$, and OH.

18. The method of claim 8, wherein all substituents of B are $C_{1-3}$ alkyl, Cl, F, or hydroxylakyl.

19. The method of claim 8, wherein B is dichlorophenyl.

* * * * *